(12) United States Patent
Graham et al.

(10) Patent No.: US 6,902,574 B2
(45) Date of Patent: Jun. 7, 2005

(54) TEMPERATURE THERAPY APPARATUS

(75) Inventors: Thomas J. Graham, Cockeysville, MD (US); James D. Israel, Somerset, NJ (US)

(73) Assignee: EBI, L.P., Parsippany, NJ (US)

( * ) Notice: Subject to any disclaimer, the term of this patent is extended or adjusted under 35 U.S.C. 154(b) by 166 days.

(21) Appl. No.: 10/352,308

(22) Filed: Jan. 27, 2003

(65) Prior Publication Data

US 2004/0147990 A1 Jul. 29, 2004

(51) Int. Cl.$^7$ ................................................ A61F 7/00
(52) U.S. Cl. .................... 607/111; 607/96; 607/108; 607/112; 607/114
(58) Field of Search ..................... 607/108, 111, 607/112, 114, 96; 62/259.3, 530, 4; 602/21.64; 2/158, 917, 16, 169, 20; 128/878, 879

(56) References Cited

U.S. PATENT DOCUMENTS

| | | | |
|---|---|---|---|
| 374,676 A * | 12/1887 | Helfaer | 2/158 |
| 3,632,966 A | 1/1972 | Arron | 219/211 |
| 4,021,640 A | 5/1977 | Gross et al. | 219/211 |
| 4,102,049 A * | 7/1978 | Harth | 33/1 B |
| 4,753,240 A | 6/1988 | Sparks | 128/379 |
| 4,961,418 A | 10/1990 | McLaurin-Smith | 128/157 |
| 5,350,418 A * | 9/1994 | Janevski et al. | 607/111 |
| 5,369,807 A | 12/1994 | Cho et al. | 2/159 |
| 5,415,624 A | 5/1995 | Williams | 602/21 |
| 5,496,358 A | 3/1996 | Rosenwald | 607/108 |
| 5,728,059 A * | 3/1998 | Wiesemann et al. | 602/64 |
| 5,879,315 A | 3/1999 | Mosley | 602/14 |
| 5,935,157 A * | 8/1999 | Harmon | 607/111 |
| 6,013,044 A | 1/2000 | Estwanik | 602/64 |
| 6,093,165 A | 7/2000 | Estwanik | 602/64 |
| 6,142,966 A | 11/2000 | Hely | 602/64 |
| 6,165,148 A | 12/2000 | Carr-Stock | 602/21 |
| 6,293,919 B1 | 9/2001 | Manente | 602/21 |

* cited by examiner

Primary Examiner—Beverly M. Flanagan
Assistant Examiner—Matthew Kasztejna
(74) Attorney, Agent, or Firm—Harness, Dickey & Pierce, P.L.C.

(57) ABSTRACT

An apparatus for applying a temperature therapy to a hand includes an outer member and an inner member. The inner member functions to at least temporarily maintain a therapy temperature. In one embodiment, the therapy temperature is less than an ambient temperature. The outer member receives the inner member and defines a pocket for receiving a thumb of the hand. The outer member includes a feature for selectively attaching to the hand and further provides for use by either a right or a left hand.

20 Claims, 5 Drawing Sheets

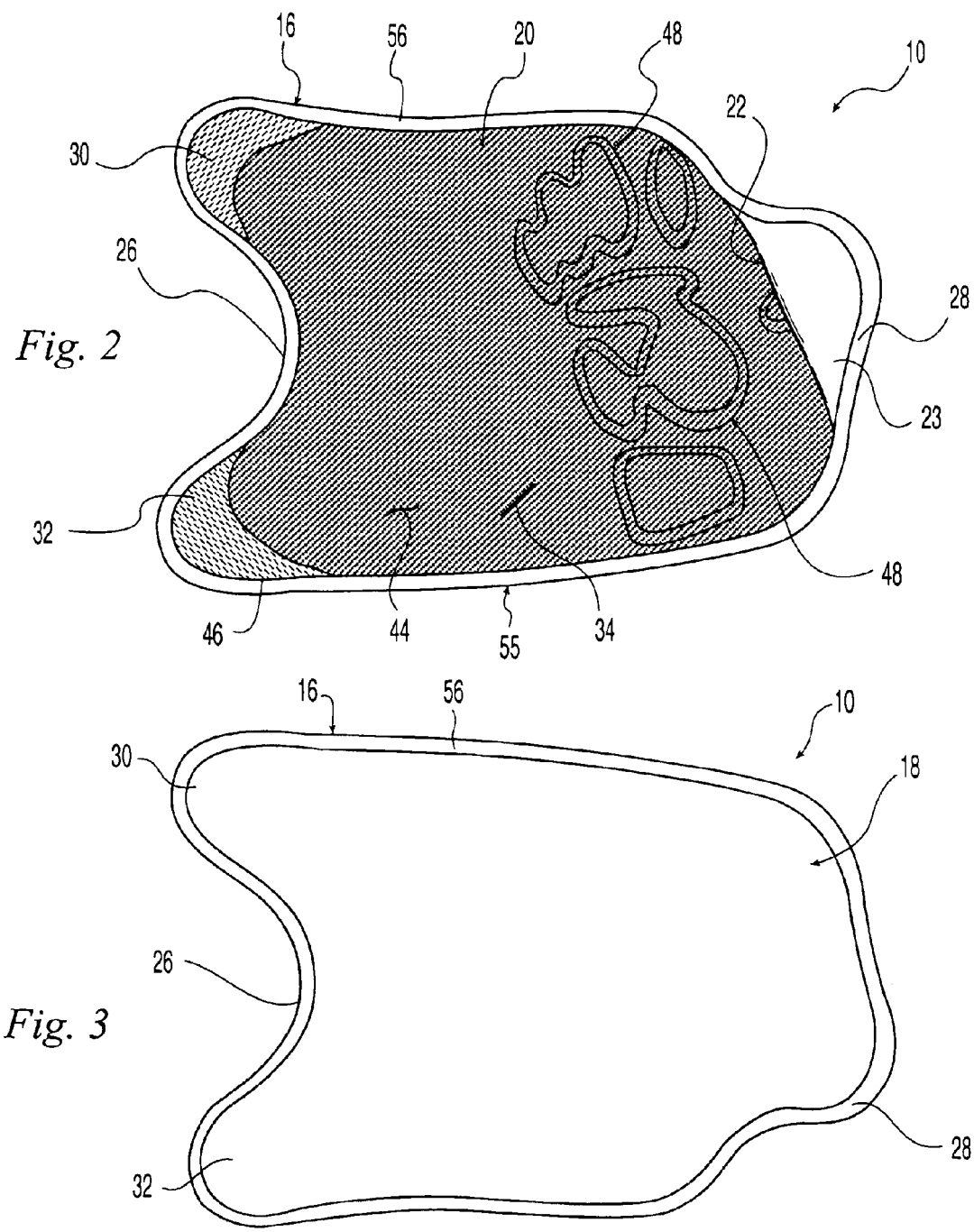

TEMPERATURE THERAPY APPARATUS

FIELD OF THE INVENTION

The present invention relates generally to an apparatus and a method for applying temperature therapy to human tissue and more particularly to an apparatus and method for applying temperature therapy to a human hand and wrist.

BACKGROUND OF THE INVENTION

Injuries to the hand through athletic activity, labor, or accident and post-operative healing involves tissue damage, pain, and swelling. To mitigate the pain and promote healing, temperature therapy is often used after surgery and in combination with other medical treatments such as in an orthopedic therapy programs and sports medicine programs. Temperature therapy is also used to treat degenerative conditions such as arthritis and inflammatory diseases and disorders.

Temperature therapy conventionally involves the application of heat or cold to tissue in an effort to heal and rehabilitate injuries such as bruises, sprains, or other trauma to bone, muscle, ligaments, tendons, and skin and to treat degenerative conditions and inflammatory diseases and disorders. In a cold application, a cold apparatus is applied to an affected area to diminish swelling and inflammation to resultantly reduce pain and promote healing of injured tissue.

In a heat application, a heated apparatus is applied to an affected area to loosen extremity tissue and joint tissue, such as muscles, ligaments and tendons. Application of heat promotes repair and healing by increasing the temperature of the affected area, thereby increasing the flow of blood and oxygen to the tissue and increasing respiration. In this manner, the application of heat serves to increase the range of motion and improve the flexibility in the patient's extremity, thus improving the functionality, comfort and performance of the injured or infirm hand or wrist.

Various devices are known in the pertinent art for delivering temperature therapy to the hand. Conventional temperature therapy devices are able to adequately provide a source of heat or cold but most are unable to uniformly deliver the temperature across the hand and therefore do not reach all injuries sufficiently. Conventional temperature therapy devices include ice packs and hot water bottles. Ice packs are typically used for the application of cold therapy and hot water bottles are used for the application of heat therapy. Ice packs, while adequately supplying a cold temperature, generally fail to do so in a uniform manner. Specifically, an ice pack is commonly a rigid body and as such does not conform to the generally complex contour of a human hand. Further, the conventional ice pack may not provide a uniform temperature to afflicted portions of the hand. In this regard, some areas may receive very cold temperatures while other areas remain out of contact with the ice pack altogether.

Hot water bottles, while adequately supplying heat to a treatment area, fail to do so in a uniform and convenient manner. While a hot water bottle generally includes a flexible outer shell, maintaining the outer surface of the bottle in contact with the hand is a difficult task. Specifically, because hot water bottles do not offer a way of selectively attaching the bottle to the hand, the patient is required to maintain the bottle in a static position to ensure that proper application of heat is achieved in a uniform manner. Further, because the hot water bottle is typically not able to wrap around the hand, it is difficult to apply heat to both sides of a hand at the same time.

It is well known that heat and cold pads are available for use in thermal therapy in place of the rigid cold pack and the cumbersome hot water bottle. While conventional heat and cold pads are typically flexible and thus better conform to the human hand than the aforementioned hot water bottle and ice pack, conventional heat and cold pads generally do not provide for a convenient method by which to apply a uniform thermal therapy treatment to an affected area. For example, while a heat and cold pad is commonly more flexible than a hot water bottle or an ice pack, conventional heat and cold pads do not provide an apparatus by which to selectively secure the pad to the hand. In this manner, conventional heat and cold pads suffer from the disadvantage of requiring the patient to maintain a constant pressure on the pack to ensure that the relationship of the pad to the hand is maintained. By requiring a patient to maintain a constant pressure on the thermal pack reduces the probability of a uniform distribution of therapy throughout the hand.

The known art also includes mitt or glove like devices for delivering a cold temperature to the hand. Such devices are shown in U.S. Pat. Nos. 5,935,157 and 6,164,413. These devices are not suitable for a wide range of hand sizes. Furthermore, these devices are not practical to pull over a severely injured or post-operative hand.

Therefore, a temperature therapy apparatus that wraps around the hand and is capable of supplying a uniform heat or cold therapy to the hand is desirable in the pertinent art. Further, supplying a temperature therapy apparatus having the ability to be selectively attached to left hands and right hands of various sizes is also desirable in the pertinent art.

SUMMARY OF THE INVENTION

It is a general object of the present invention to provide an apparatus for delivering temperature therapy to a hand that overcomes the disadvantages of the prior art, including but not limited to those addressed above.

It is another object to provide an apparatus for delivering cold therapy to a hand that wraps around the hand.

It is another object of the present invention to provide an apparatus for providing therapy in a uniform manner such that the entire afflicted portion of the hand receives treatment.

It is a related object of the present invention to provide a flexible (i.e., malleable) device capable of being used on either a right hand or a left hand of various sizes, while uniformly applying a temperature therapy.

It is another object of the present invention to provide a reusable temperature therapy apparatus that can be used to either deliver a source of heat or cooling to a hand or wrist.

In one aspect, the present invention provides an apparatus for applying a temperature therapy having a flexible pad for wrapping around a hand. The flexible pad includes an inner member for applying the temperature therapy to the hand and an outer member having an inner side for receiving the hand and an outer side for selective attachment to the hand. The inner member of the hand maintains a therapy temperature greater or less than an ambient temperature. The outer member receives the inner member and generally defines a pocket for receiving a thumb of the hand. The outer member includes a feature for selectively attaching to the hand and further provides for use by either a right or a left hand.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is a view of an inner side of the temperature therapy apparatus of FIG. 1.

FIG. 3 is a view of the outer side of the temperature therapy device of FIG. 1.

DETAILED DESCRIPTION OF THE PREFERRED EMBODIMENTS

Figure 1:
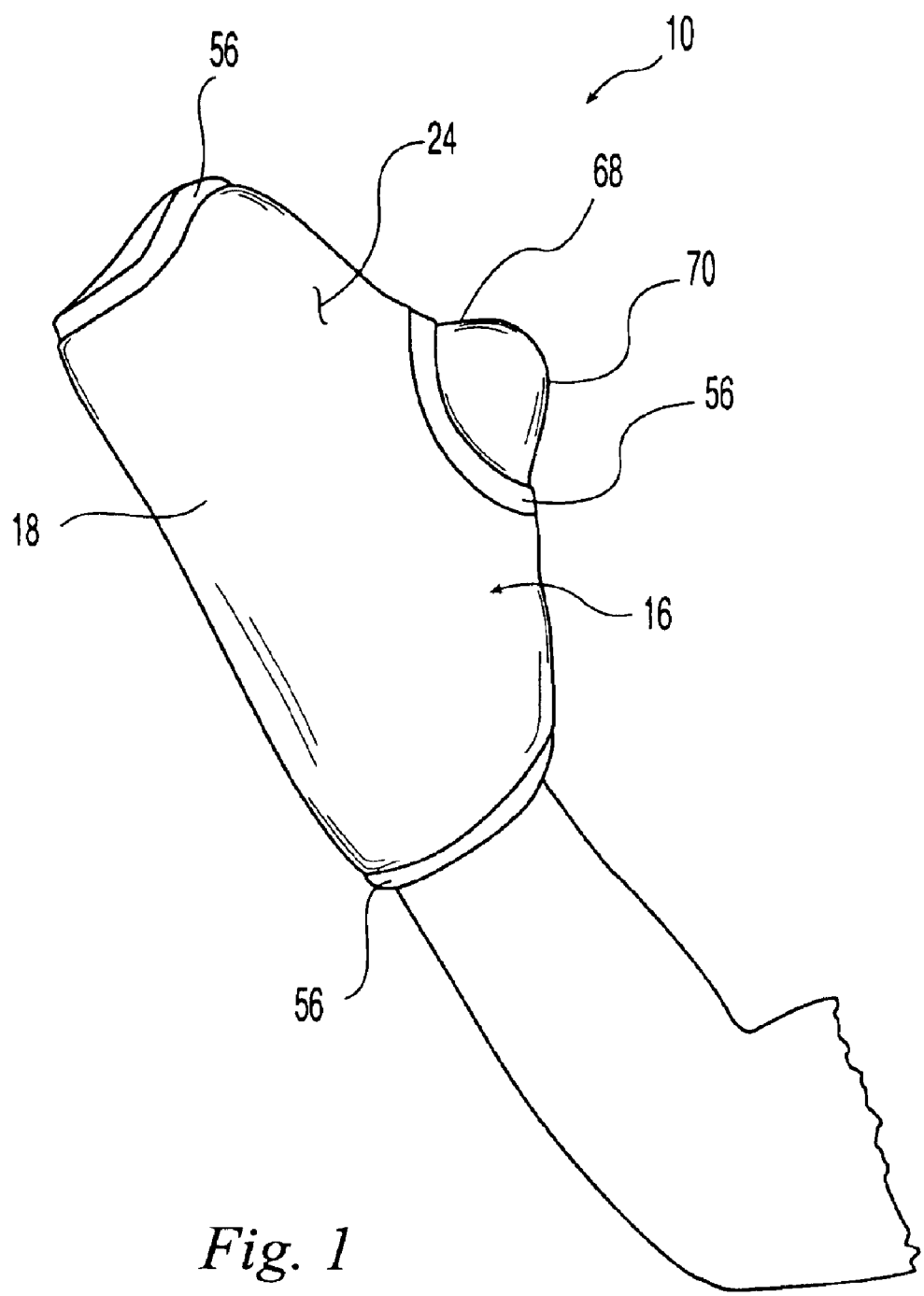
FIG. 1 is a perspective view of an apparatus for providing temperature therapy to a hand shown operatively associated with a hand and wrist.

The following description of the preferred embodiment is merely exemplary in nature and is in no way intended to limit the invention, its application, or uses.

With reference to FIGS. 1–4 of the drawings, an apparatus constructed in accordance with the teachings of the preferred embodiment of the present invention is illustrated and generally identified at reference character 10. The flexible pad 10 is specifically intended for use in applying temperature therapy to a hand 12 (see FIGS. 5 and 6). The apparatus is shown in the form of a flexible pad 10 and generally includes an inner member or bladder 14 and an outer member or cover 16. Insofar as the present invention is concerned, the inner member 14 conventionally functions to maintain a therapy temperature greater or less than an ambient temperature. The outer member 16 functions to support the inner member 14 and selectively holds the inner member 14 in engagement with the hand 12.

With particular reference to FIGS. 2 and 3, the outer member 16 is shown to generally include a first or outer side 18, a second or inner side 20, and a pocket 22. In the embodiment illustrated, the first side 18 is defined by a fabric layer. The first side 18 may include a first surface 24 having a temperature barrier integrally formed with the fabric to prevent heat or cold from radiating through the first side 18. In this manner, the first surface 24 acts to direct a temperature generally away from the outer surface 24, thereby ensuring that a temperature generated by the inner member is not lost through the outer surface 24 of the first side 18. The first and second sides 18 and 20 are joined along a substantial portion of their peripheries by a seam or band 56.

As will become more appreciated below, the apparatus 10 is particularly configured to receive the hand 12 with the thumb in an extended orientation. To facilitate this orientation, the outer member 16 includes a laterally extending portion 28. The outer member 16 further includes a recess 26 along a side laterally opposite the extension 28. The recess 26 is adapted to receive the extension 28 when the apparatus 10 is wrapped around the hand 12 and is formed between first and second flaps 30 and 32. The materials of the pad 10 have the requisite ability to conform to the generally complex structure of a hand 12.

The layers of the inner side 20 of the outer member 16 are adapted to transmit the temperature from the inner member 14 without creating a drastic or painful condition for the hand 12. In the preferred embodiment, the mesh layer of the inner side 20 includes a plurality of holes 46 such that the temperature passing from the inner member 14 through the inner side 20 is efficiently transmitted to the hand 12. In this manner, the inner side 20 serves to protect the hand 12 from an extreme temperature which could cause pain or discomfort while permitting an adequate amount of temperature to pass through the inner side 20 and reach the hand 12. While a mesh material is disclosed, it should be understood that any suitable material which allows for heat or cold to pass to the hand 12 while concurrently protecting the hand 12 from extreme temperatures is anticipated and should be considered as part of the present invention.

Figure 5:
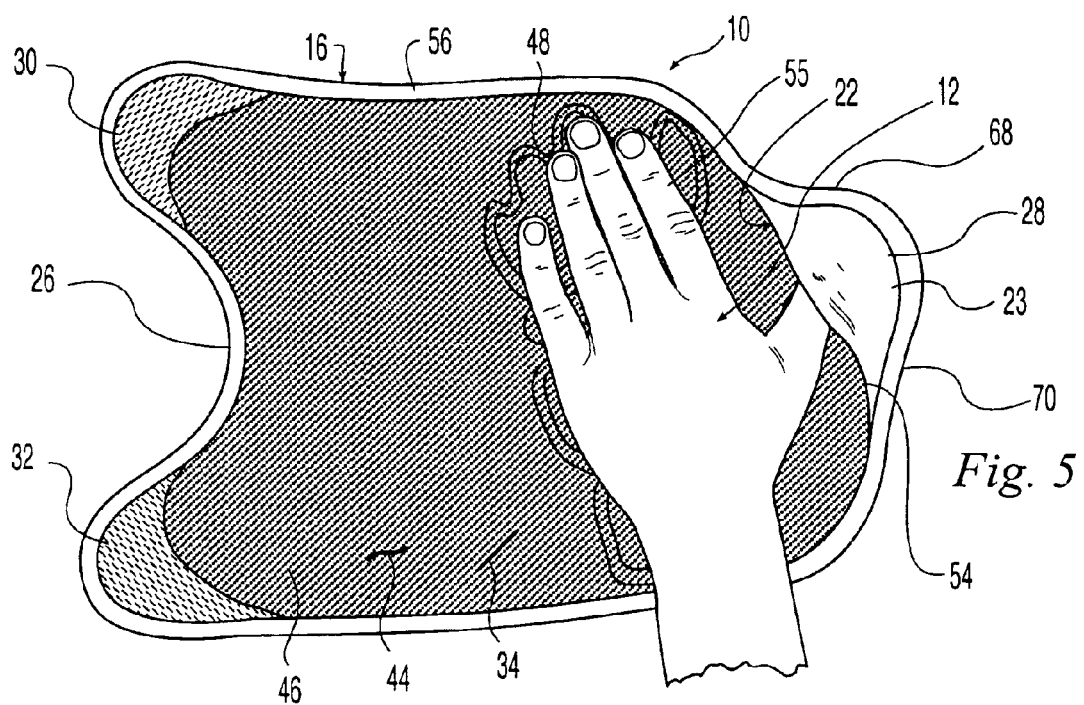
FIG. 5 is a view similar to FIG. 2 illustrating an initial step in applying the temperature therapy apparatus to a right hand.
Figure 6:
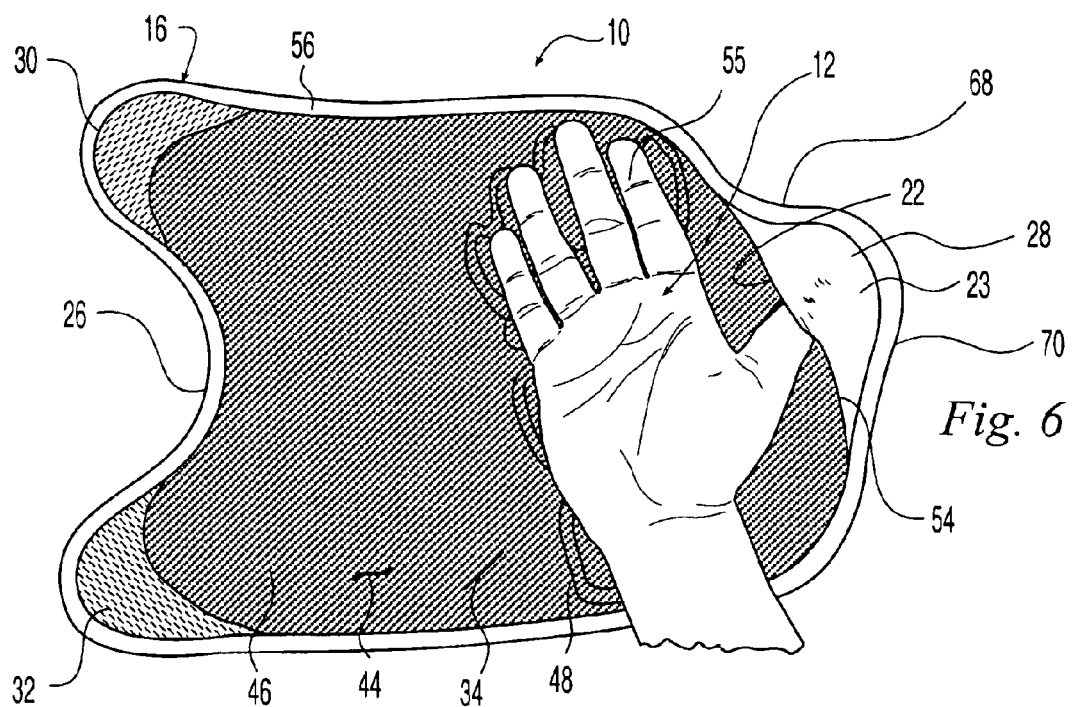
FIG. 6 is a view similar to FIG. 2 illustrating an initial step in applying the temperature therapy apparatus to a left hand.
Figure 7:
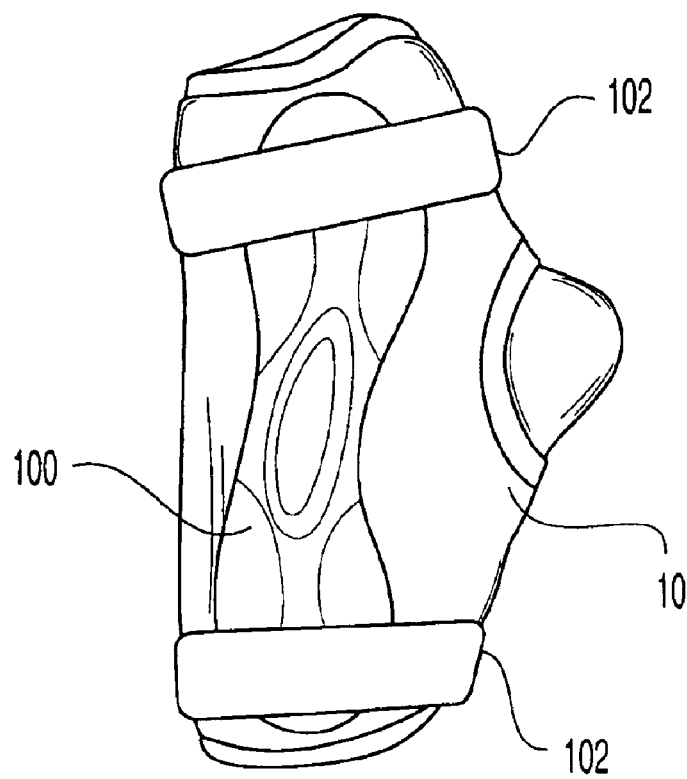
FIG. 7 is an environmental view illustrating the apparatus for providing temperature therapy of the present invention shown operatively associated with a stay.
Figure 8:
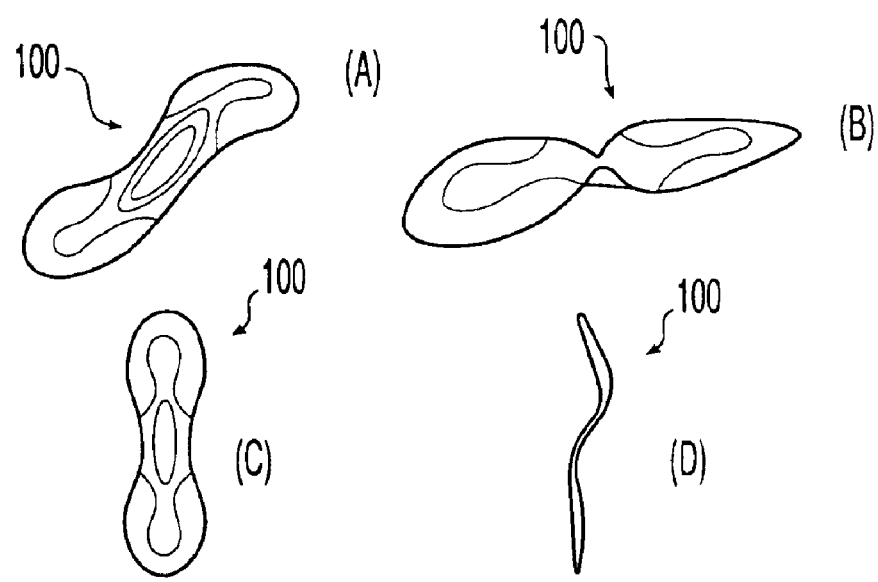
FIGS. 8(a)–8(d) are various views of the stay of FIG. 7 shown removed from the apparatus for purposes of illustration.

In the embodiment illustrated, the fabric layer of the inner side 20 is imprinted with an outline 48 of a human hand. The outline 48 assists a patient in correctly orienting the pad 10 with a hand 12. The outline 48 is operable to assist in selectively aligning either a right or a left hand depending upon the desired application and required treatment. The outline 48 is visible through the holes 46 of the mesh layer. Alternatively, the outline 48 can be formed integral with the generally mesh layer structure or can be applied directly to the mesh layer by a suitable means such as, but not limited to, screen printing and the like. FIG. 5 depicts a left hand 12 utilizing the outline 48 to properly align a left hand with the pad 10. FIG. 6 depicts a right hand 12 utilizing the outline 48 to properly align a right hand with the pad 10.

The apparatus 10 of the present invention further includes an arrangement for fastening the apparatus 10 to the hand. In the embodiment illustrated, the fastening arrangement is a hook and loop type fastening arrangement such as those sold under the registered trademark Velcro®. Specifically, the fabric of the outer side 18 of the outer member 16 is a looped fabric adapted to cooperatively and temporarily engage such hooks. The portion of the inner side 20 of the outer member 16 that define the flaps 30 and 32 each carry a hooked material portion for mating engagement with the loops (not particularly shown) of the outer side 18 such that contact between the outer side 18 and the hooked material portions causes the hooks to engage the loops, thereby allowing the pad 10 to be selectively attached to a hand 12, as will be discussed further herein below. It should be understood that while interaction between a plurality of hooks and loops is disclosed, any suitable means for selectively attaching the first and second flaps 30 and 32 to the outer side 18 such as by way of a snap or button, is anticipated and should be considered within the scope of the present invention.

Referring specifically to FIG. 2, the pocket 22 is disposed opposite the first and second flaps 30 and 32. The pocket 22 is defined by flexible material 23 such as fabric so as to conform to a thumb 54 inserted therein. The pocket 22 serves to constrict the thumb 54 between the inner side 20 and the pocket material 23 in an effort to both guide the hand 12 into proper alignment relative to the pad 10 and to constrict the hand 12, thus preventing relative movement of the hand 12 relative the pad 10 once secured.

As previously discussed, the inner member 14 is received by the outer member 16. In this manner, the inner member 14 can be selectively removed and inserted into the outer member 16. To accommodate the inner member 14, the outer member 16 defines a pouch or cavity (shown partially at reference element 55 in FIG. 2). The first and second sides 18 and 20 are fixedly attached to one another by the outer band 56 that encircles an outer perimeter of the first and second sides 18 and 20. The band 56 serves to maintain the cavity 55 by fixedly attaching the first and second sides 18 and 20 by a suitable means such as stitching or epoxy. In addition to fixedly attaching the first and second sides 18 and 20, the band 56 provides the outer perimeter of the pad 10 with a uniform and smooth appearance.

The band 56 further prevents the temperature as generated by the inner member 14 from escaping the pad 10, thereby ensuring that more temperature therapy is received by the hand 12. The band 56 also provides an access slot adjacent a lower side of the pad 10 for insertion and removal of the inner member 14. Specifically, the slot provides access to the cavity 55 so that the inner member 14 can be removed in the event that the inner member 14 requires replacement, or the outer member 18 requires cleaning.

As best shown in FIG. 2, the band 56 further serves to fixedly attach the pocket material 23 to the inner side 20 such that the material 23 is constrained along an outer perimeter of the pad 10 and open at one end for receiving a thumb 54. In this manner, the band 56 secures the pocket material 23 to the remainder of the pad 10, thereby creating the pocket 22 for receiving a thumb 54. Effectively, the thumb 54 is received between the pocket material 23 and the inner side 20, as will be discussed further below and as best shown in FIGS. 5 and 6.

Figure 4:
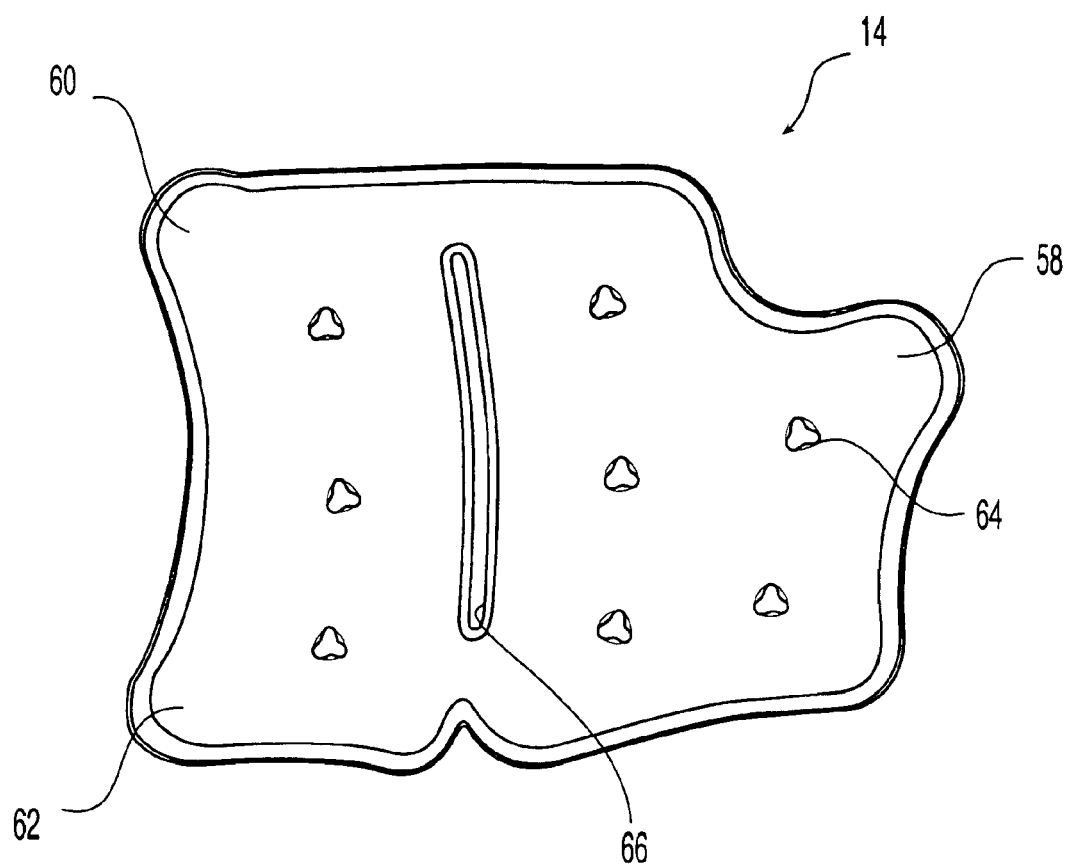
FIG. 4 is a bladder of the temperature therapy apparatus.

With particular reference to FIG. 4, the inner member 14 is shown in further detail. In the embodiment illustrated, the inner member 14 is adapted to at least temporarily maintain a therapy temperature that is less than an ambient temperature. Alternatively, it will be appreciated by those skilled in the art that the inner member may be adapted to maintain a therapy temperature that is greater than the ambient temperature.

The inner member 14 is illustrated to include first, second, and third extensions, 58, 60, and 62. The first extension 58 is received by the extension 28 disposed generally near the pocket 22 while the second and third extensions 60 and 62 are received by the first and second flaps 30 and 32, respectively. In this manner, the inner member 14 is effectively constrained between the recess 26 and the extension 28. The inner member 14 further includes a plurality of ribs 64 to aid in increasing the overall flexibility of the pad 10 and a central rib 66 to aid in bending the inner member 14 around hand 12. The inner member 14 may be quickly chilled and functions to maintain a therapy temperature of approximately 45°–50° for up to about twenty minutes.

With particular reference to FIGS. 1, 5, and 6, the operation of the pad 10 will now be described in further detail. To provide a hand 12 with a thermal therapy, the inner member 14 must first be either heated or cooled, depending on the particular application. In one embodiment, the inner member 14 can be heated or cooled while disposed in the outer member 16. In another embodiment, the inner member 14 must be removed from the outer member 16 through the slot to be heated or cooled. In cases where the inner member 14 requires external heating or cooling, the pad 10 cannot be applied to the hand 12 until the inner member 14 reaches a predetermined temperature. Once the inner member 14 reaches the desired temperature, it may then be inserted into the outer member 16 though the slot such that the first extension 58 is aligned with extension 28 and the first and second extensions 60 and 62 are aligned with the flaps 30 and 32.

Once the inner member 14 reaches the desired temperature, and is properly disposed within the outer member 16, the pad 10 can be applied to the hand 12. To properly wrap the pad 10 around the hand 12, the hand 12 is first placed on the pad 10 and aligned with the outline 48. Specifically, the thumb 54 of either a right or left hand 12 is inserted into the pocket 22 while the fingers 55 are overlaid on the outline 48 as best shown in FIGS. 5 and 6. At this point, the pad 10 may be wrapped around the hand 12.

To wrap the pad 10, the first flap 30 is generally brought over the hand 12 such that the first engagement surface 50 contacts the outer surface 24 adjacent a first side 68 the pocket 22 and the second flap 32 is brought across the hand such that the second engagement face 52 engages the first surface 24 on a second side 70 of the pocket 22 as best shown in FIG. 1. In this manner, the hooks of the first and second engagement faces 50 and 52 engage the loops of the outer surface 18 to selectively hold the pad 10 in the wrapped position.

Once the pad 10 is secured to the hand 12, the temperature therapy is applied to the entire hand 12 through the inner member 14 emitting either cold or heat through the second and third surfaces 34 and 44. It should be noted that the temperature released by the inner member 14 is effectively captured by the outer surface 24 and held in contact with the hand due to the temperature barrier integrally formed with the first surface 24. In this manner, the pad, 10 maintains a temperature therapy over an extended period of time by effectively trapping the heat or cold within the pad 10.

With reference to FIG. 7 and FIGS. 8(a)–8(d), a rigid stay 100 for use with the pad 10 is illustrated. In certain applications, it may be desirable to secure the rigid stay 100 to the pad 10 for purposes of maintaining the hand and wrist in a preferred position. Such a preferred position is commonly referred to in the art as an "intrinsic plus position". In the preferred embodiment, the stay 100 is constructed of a rigid plastic. As shown in the environmental view of FIG. 7, the stay 100 may be secured to the pad 10 with Velcro® members 102. Alternatively, the stay 100 may be secured to the pad with elastic bands 102 or in any other manner well known in the art.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A flexible apparatus for wrapping around a hand and applying a temperature therapy to the hand, the flexible apparatus comprising:

an inner member for at least temporarily maintaining a therapy temperature;

an outer member having inner and outer sides and receiving the inner member therebetween, the inner side including first and second portions orientable substantially co-planarly;

a pocket defined over a portion of the inner side for receiving a thumb of the hand;

the inner member and outer member cooperating to define a flexible pad such that the inner side can be wrapped around the hand for positioning the first portion adjacent a palm of the hand and the second portion adjacent a back of the hand.

2. The flexible apparatus for wrapping around a hand and applying a temperature therapy to the hand of claim 1, wherein the pocket is positioned to selectively receive the thumb of a right hand and the thumb of a left hand.

3. The flexible apparatus for wrapping around a hand and applying a temperature therapy to the hand of claim 2, wherein the left hand is positioned selectively in one of a palm-down orientation or a palm-up orientation for receiving the thumb of the left hand and the right hand is positioned in the other of the palm-up and palm-down orientation when receiving the thumb of the right hand.

4. The flexible apparatus for wrapping around a hand and applying a temperature therapy to the hand of claim 2, wherein the left hand is positioned in a palm-down orientation for receiving the thumb of the left hand and the right hand is positioned in the palm-up orientation when receiving the thumb of the right hand.

5. The flexible apparatus for wrapping around a hand and applying a temperature therapy to the hand of claim 1, wherein a portion of the inner member is positioned proximate to the thumb when the flexible pad is wrapped around the hand.

6. The flexible apparatus for wrapping around a hand and applying a temperature therapy to the hand of claim 1, further comprising a fastening arrangement for securing the flexible pad to the hand.

7. The flexible apparatus for wrapping around a hand and applying a temperature therapy to the hand of claim 6, wherein the fastening arrangement is a hook and loop type fastening arrangement.

8. The flexible apparatus for wrapping around a hand and applying a temperature therapy to the hand of claim 6, wherein the fastening arrangement includes a hooked material positioned on at least a portion of one of the inner and outer sides of the flexible pad and a cooperating looped material positioned on at least a portion of the other of the inner and outer sides.

9. The flexible apparatus for wrapping around a hand and applying a temperature therapy to the hand of claim 8, wherein the hooked material is positioned adjacent a first edge of the flexible pad and the pocket is positioned a second, opposite edge of the flexible pad.

10. The flexible apparatus for wrapping around a hand and applying a temperature therapy to the hand of claim 1, wherein the inner side of the flexible pad includes a hand outline for selectively receiving and properly positioning a selected one of a right hand and a left hand.

11. The flexible apparatus for wrapping around a hand and applying a temperature therapy to the hand of claim 10, wherein a thumb outline of the hand outline at least partially extends into the pocket.

12. The flexible apparatus for wrapping around a hand and applying a temperature therapy to the hand of claim 1, wherein the therapy temperature is less than an ambient temperature.

13. A method of applying a temperature therapy to a hand, the method comprising:
providing a flexible pad including an inner member and an outer member, the outer member having inner and outer sides and receiving the inner member therebetween, the inner side having first and second portions and defining a pocket for receiving a thumb of the hand;
maintaining the inner member at a therapy temperature;
orienting the first portion substantially coplanarly to the second portion;
positioning the hand adjacent the inner side with the thumb of the hand extending at least partially into the pocket;
wrapping the flexible pad around the hand such that the first portion of the inner side is positioned adjacent a palm of the hand and the second portion of the inner side is positioned adjacent a back of the hand; and
securing the flexible pad to the hand.

14. The method of applying a temperature therapy to a hand of claim 13, further comprising positioning the pocket on the outer member to selectively receive the thumb of a right hand and the thumb of a left hand.

15. The method of applying a temperature therapy to a hand of claim 13, wherein positioning the hand adjacent the inner side with a thumb of the hand in the pocket includes positioning the thumb proximate a portion of the inner member.

16. The method of applying a temperature therapy to a hand of claim 13, wherein positioning the hand adjacent the inner side with a thumb of the hand in the pocket includes positioning the hand selectively in one of palm-down orientation or a palm-up orientation if the hand is a left hand or positioning the hand in the other of the palm-down orientation and palm-up orientation if the hand is a right hand.

17. The method of applying a temperature therapy to a hand of claim 13, wherein securing the flexible pad to the hand includes the step of securing a portion of the inner side to a portion of the outer side.

18. The method of applying a temperature therapy to a hand of claim 17, wherein the portion of the inner side includes one of a hooked material and a cooperating looped material and the outer side includes the other of the hooked material and the cooperating looped material.

19. The method of applying a temperature therapy to a hand of claim 13, wherein the step of maintaining the inner member and a therapy temperature includes maintaining the inner member and a therapy temperature less than an ambient temperature.

20. A flexible apparatus for wrapping around a hand and applying a temperature therapy to the hand, the flexible apparatus comprising:
an inner member for at least temporarily maintaining a therapy temperature;
a hollow outer member having inner and outer sides and receiving the inner member therebetween; and
a pocket defined over a portion of the inner side for receiving a thumb of the hand,
wherein the inner member and outer member cooperate to define a flexible pad such that the inner side of the outer member can be wrapped around the hand with the thumb received in the pocket of the inner side of the outer member.

* * * * *